(12) United States Patent
Sampei (10) Patent No.: US 8,933,399 B2
(45) Date of Patent: Jan. 13, 2015

(54) MASS SPECTROMETRY DEVICE INCLUDING SELF-CLEANING UNIT

(75) Inventor: Makoto Sampei, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/123,310

(22) PCT Filed: Apr. 9, 2012

(86) PCT No.: PCT/JP2012/059681
§ 371 (c)(1),
(2), (4) Date: Dec. 26, 2013

(87) PCT Pub. No.: WO2012/165053
PCT Pub. Date: Dec. 6, 2012

(65) Prior Publication Data
US 2014/0103207 A1 Apr. 17, 2014

(30) Foreign Application Priority Data

Jun. 3, 2011 (JP) .................................. 2011-124764

(51) Int. Cl.
*H01J 49/40* (2006.01)
*H01J 49/10* (2006.01)
(Continued)

(52) U.S. Cl.
CPC ........... *H01J 49/02* (2013.01); *H01J 37/32935* (2013.01); *G01N 27/624* (2013.01);
(Continued)

(58) Field of Classification Search
CPC . G01N 27/624; G01N 15/0266; G01N 33/18; G01N 33/24; G01N 33/483; H01J 49/0018; H01J 49/04; H01J 49/067; H01J 49/14; H01J 49/165; H01J 49/168; H01J 49/162; H01J 49/145; H01J 49/107; H01J 49/10; H01J 49/0468; H01J 49/02; H01J 49/0077; H01J 49/0013; H01J 37/32935; H01J 37/32; H01J 37/32422; H01J 37/32862

USPC ............. 250/288, 282, 287, 281, 286, 423 R, 250/290, 292, 424, 293, 423 P, 283, 2, 85, 250/289, 291, 294, 299, 423 F, 425, 427, 250/492.2

See application file for complete search history.

(56) References Cited

U.S. PATENT DOCUMENTS 6,170,492 B1  1/2001 Ueda et al.
6,192,898 B1 * 2/2001 Aitani et al. ................... 134/1.1
(Continued)

FOREIGN PATENT DOCUMENTS

JP       10-125276 A    5/1998
JP     2001-502114 A    2/2001
(Continued)

*Primary Examiner* — David A Vanore
(74) *Attorney, Agent, or Firm* — Mattingly & Malur, PC (57) ABSTRACT

When a specimen from a specimen ionizing unit is not sufficiently ionized, is caused to remain in sites other than a pore in an introducing section and be deposited as a product such as an oxide or carbide, which causes a deterioration in the performance of the mass spectrometry device. The mass spectrometry device has a specimen ionizing section for ionizing a specimen, a specimen-introduction regulating chamber into which ions of the ionized specimen are introduced, a differential evacuation chamber located downstream of the specimen-introduction regulating chamber, and an analyzing section located at the downstream side of the differential evacuation chamber, in which a discharge generating means is formed for generating an electric discharge inside the specimen-introduction regulating chamber and/or the differential evacuation chamber. The discharge generating means has a specimen introducing section electrode and a first-pore-section-forming member located oppositely to each other inside the specimen-introduction regulating chamber.

8 Claims, 8 Drawing Sheets

(51) Int. Cl.
- *G01N 33/18* (2006.01)
- *H01J 49/02* (2006.01)
- *H01J 37/32* (2006.01)
- *G01N 27/62* (2006.01)
- *H01J 49/06* (2006.01)

(52) U.S. Cl.
CPC .................................... *H01J 49/067* (2013.01)
USPC ........... 250/288; 250/281; 250/282; 250/286; 250/423 P (56) References Cited

U.S. PATENT DOCUMENTS

| | | | |
|---|---|---|---|
| 6,380,538 B1 | 4/2002 | Bajic | |
| 6,518,567 B1* | 2/2003 | Ganeev et al. | 250/282 |
| 6,544,484 B1* | 4/2003 | Kaufman et al. | 422/186.04 |
| 6,794,646 B2* | 9/2004 | Tong et al. | 250/288 |
| 6,806,463 B2* | 10/2004 | Miller et al. | 250/286 |
| 7,005,634 B2* | 2/2006 | Shiokawa et al. | 250/288 |
| 7,030,372 B2* | 4/2006 | Miller et al. | 250/287 |
| 7,399,959 B2* | 7/2008 | Miller et al. | 250/287 |
| 7,411,186 B2* | 8/2008 | Mordehai | 250/288 |
| 7,453,059 B2* | 11/2008 | Koo et al. | 250/287 |
| 7,476,849 B2* | 1/2009 | Koo et al. | 250/287 |
| 8,669,518 B2* | 3/2014 | Ishiguro et al. | 250/282 |
| 2002/0139930 A1 | 10/2002 | Shiokawa et al. | |
| 2009/0014644 A1 | 1/2009 | Yang et al. | |
| 2012/0248301 A1* | 10/2012 | Short et al. | 250/282 |
| 2013/0260478 A1* | 10/2013 | Ewing et al. | 436/501 |
| 2014/0103207 A1* | 4/2014 | Sampei | 250/288 |

FOREIGN PATENT DOCUMENTS

| | | |
|---|---|---|
| JP | 2002-518841 A | 6/2002 |
| JP | 2002-298776 A | 10/2002 |
| JP | 2004-362903 A | 12/2004 |
| JP | 2008-130390 A | 6/2008 |
| JP | 2008-209312 A | 9/2008 |
| JP | 2010-533933 A | 10/2010 |
| JP | 2011-102763 A | 5/2011 |

* cited by examiner

MASS SPECTROMETRY DEVICE INCLUDING SELF-CLEANING UNIT

TECHNICAL FIELD

The present invention relates to a mass spectrometry device having a self-cleaning unit using high frequencies.

BACKGROUND ART

A mass spectrometry device will be described, giving, as an example thereof, an automatic or manual mass spectrometry device of ionizing a specimen from a specimen generating section of the device, introducing the ionized specimen into a specimen introducing section of the device, and identifying or analyzing the specimen in an analyzing section thereof.

In the mass spectrometry device, at the time of analyzing the introduced specimen, an energy based on a heater, a high voltage or some other is used to ionize the specimen, and then the specimen is introduced through the specimen introducing section of the mass spectrometry device. In the step of attaining the ionization, the specimen, when not sufficiently ionized, turns to a product such as an oxide or carbide near the specimen introducing section of the mass spectrometry device by an energy obtained from a heat source, such as the heater, which the mass spectrometry device has. The product is then deposited as a deposit near the specimen introducing section. This deposit narrows a pore in the specimen introducing section of the mass spectrometry device so that the introduction of the specimen is hindered. As the case may be, the deposit deposited near the specimen introducing section is electrically charged, or charged up by a potential supplied from a power supply which the mass spectrometry device has. Thus, there is similarly caused a problem that the specimen introduction is hindered.

In order to solve this problem to restore the performance of the mass spectrometry device, it is necessary to carry out a cleaning-up work of performing removal of the substance produced and deposited in the specimen introducing section of the mass spectrometry device, and other operations. Usually, for the maintenance thereof, parts of the introducing section are detached. Therefrom, the deposit is then removed by manual operations such as polishing and shaving, and is further subjected to, for example, washing with a chemical liquid or by ultrasonic waves. After the cleaning-up and other works are carried out, the detached parts are attached and further vacuum drawing and others are performed. In this way, starting-up works and other works after the maintenance of the mass spectrometry device are advanced.

In the technical background for solving such a problem of mass spectrometry devices, JP 2001-502114 A (PTL 1) is known. This publication includes the following sentences: "nonvolatile components are deposited around the injection orifice. An introducing pipe for carrying a washing liquid has an opening adjacent to the injection orifice, and gives the washing liquid onto at least one area of the front surface of the orifice member when an ion source is operated". Thus, about the self-cleaning of mass spectrometry devices, cleaning using a washing liquid is known. In other known techniques, generally, a person who carries out the maintenance of a mass spectrometry device detaches parts thereof, and performs cleaning-up works, such as removal of a deposit thereon; thereafter, the person washes the parts with, for example, a chemical liquid, and further makes other works; and subsequently the person attaches the detached parts to the device.

Similarly, mass spectrometry devices have a problem described below as a problem caused at the time of the maintenance thereof.

The mass spectrometry devices are each a vacuum device, or a device in which a heat source such as a heater is arranged in a specimen introducing section. For this reason, when the specimen introducing section is subjected to maintenance works such as cleaning-up and washing, for example, the following works are performed: the cancel of the vacuum, vacuum-drawing, the stop of the supply of electric power into the heater, which is a heat source, and re-supply of electric power. At this time, the stability of the vacuum degree, and the stability degree of the temperature of the heat source produce effects onto the supply of a stable performance of the mass spectrometry device. In order to solve such a problem, it has been becoming necessary for mass spectrometry devices that the maintenance period thereof is shortened and the robustness thereof is improved.

In order to solve such problems, there are documents disclosing that a chemical liquid is automatically supplied, such as PTL 1 described above. However, it cannot be denied that the use of the chemical liquid results in a fall in the respective stabilities of the vacuum degree and the heat source. Thus, in order to gain the stability of the device, a predetermined period is required.

CITATION LIST

Patent Literature

PTL 1: JP 2001-502114 A

SUMMARY OF INVENTION

Technical Problem

When a specimen from the specimen ionizing unit (ion source) is introduced, the specimen, if not sufficiently ionized, is caused to remain in sites other than the pore in the introducing section and then deposited as a product such as an oxide or carbide by an energy such as heat. The deposited product narrows the pore in the specimen introducing section of the mass spectrometry device, and the deposit on the surfaces of the parts are electrically charged. By these inconveniences and other causes, a problem is caused that the mass spectrometry device is deteriorated in performance. Moreover, when subjected to maintenance works such as cleaning-up and washing works, the mass spectrometry device is required to receive not only detaching and attaching works of its parts to be maintained but also detaching and attaching works of its heater, or some other component as an appendant heat source. Similarly, it is necessary to make subsidiary works, for example, works of lowering and raising the temperature of the heater or the other appendant heat source component, and works of cancelling a vacuum in the analyzing section, and attaining the vacuum-drawing thereof, and other operations.

Conventional mass spectrometry devices have the above-mentioned problems, such as deteriorations of the devices in performance by the deposit and the like, and by the matter that the temperature stability required until the devices turn into a stable state is bad, or the stability of the vacuum degree is bad.

Solution to Problem

The present invention is a mass spectrometry device including a specimen supply source, a specimen ionizing section for ionizing a specimen supplied from the specimen supply source, a specimen-introduction regulating chamber into which ions of the ionized specimen are introduced, a differential evacuation chamber located at the downstream side of the specimen-introduction regulating chamber, and an analyzing section located at the downstream side of the differential evacuation chamber, the device further including a discharge generating means for generating an electric discharge inside at least one of the specimen-introduction regulating chamber and the differential evacuation chamber.

Advantageous Effects of Invention

According to the present invention, a deposit can be decomposed and removed by discharge energy based on the electric discharge in the specimen-introduction regulating chamber or the differential evacuation chamber. This matter makes unnecessary the dismantlement and fabrication of parts of the device, the cancel of the vacuum, vacuum-drawing, and other works. The period for the maintenance thereof can be shortened. Moreover, at the time of the maintenance, the environment around the mass spectrometry device is not broken, so that after the maintenance, the device continuously keeps a stable performance in a stable environment. As a result, the device makes it possible to lighten or reduce problems based on a deterioration in the performance thereof, or on others.

DESCRIPTION OF EMBODIMENTS

Example 1

A description will be made about embodiments of the present invention, referring to the drawings.

Figure 1:
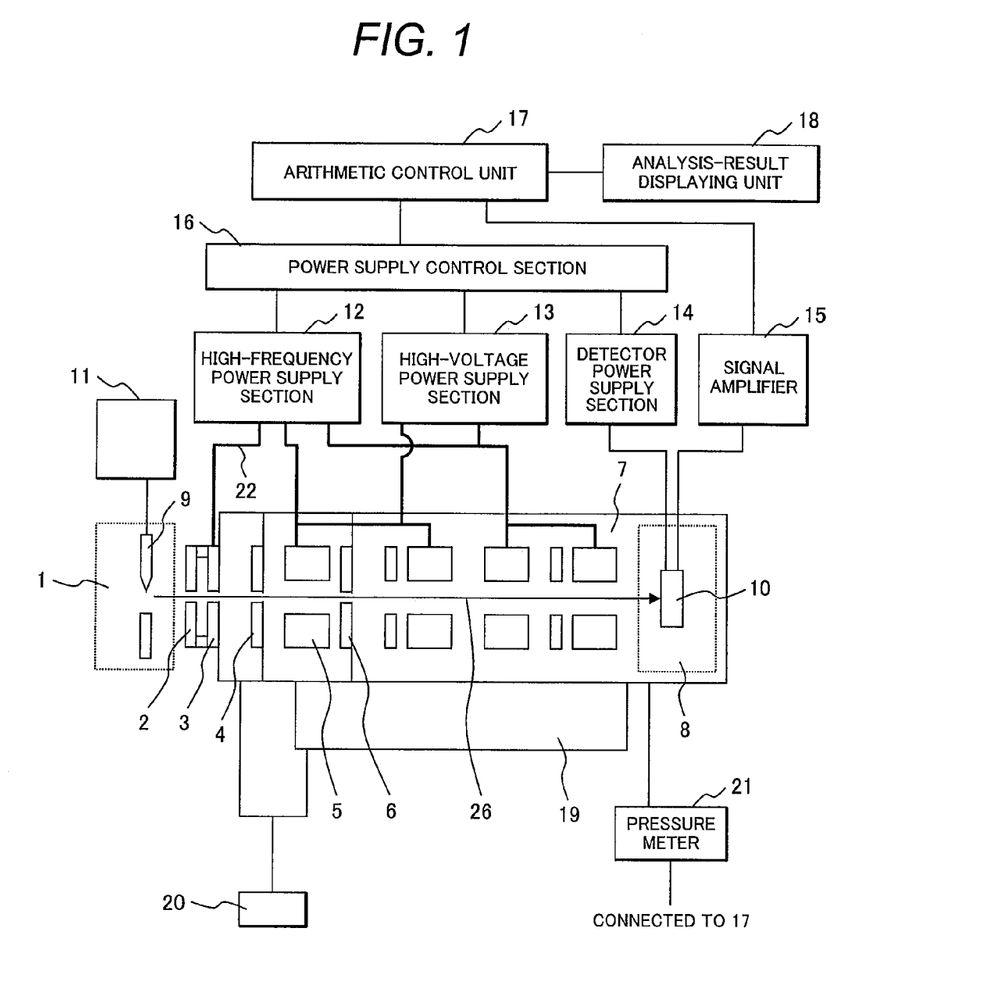
FIG. 1 is a view illustrating a structure in which a self-cleaning unit using an existent high-frequency power supply is laid out in a quadrupole mass spectrometry device in an example of the present invention.

First, FIG. 1 is a view illustrating the structure of a quadrupole mass spectrometry device which is an example of the invention.

The body of this quadrupole mass spectrometry device has a specimen introducing section electrode 2 having at the center thereof a pore, for introduction, through which a specimen ionized by a specimen ionizing unit 1 is to be introduced, a first-pore-section-forming member 3 having at the center thereof a first pore, a second-pore-section-forming member 4 having at the center thereof a second pore, a summarizing section 5, an analyzing section 7, a detecting section 8, and a detector 10 set in the detecting section 8.

The quadrupole mass spectrometry device also has a pump 20 for drawing the air in the body roughly, a high-vacuum pump 19, a pressure meter 17, and an analysis-specimen supplying section (LC) 11.

The mass spectrometry device further has an arithmetic control unit 17, a power supply control section 16, a high-frequency power supply section 12, a high-voltage power supply section 13, a detecting section power supply section 14, a signal amplifier 15, and an analysis-result displaying unit 18. A group (beam) 26 of ions is passed through the body. Reference number 22 represents a high-frequency wire for a self-cleaning unit. The self-cleaning unit (discharge generating means) is mainly composed of the specimen introducing section electrode 2, the first-pore-section-forming member 3, the second-pore-section-forming member 4, the high-frequency wire 22 for the self-cleaning unit, the arithmetic control unit 17, the power supply control section 16, the high-frequency power supply section 12, and the high-voltage power supply section 13.

For the self-cleaning unit (discharge generating means), use is made of the arithmetic control unit 17, the power supply control section 16, the high-frequency power supply section 12 and the high-voltage power supply section 13, which are some of existent units and sections which the mass spectrometry device has; and further the high-frequency wire 22 for the self-cleaning unit is laid out. In this way, the self-cleaning unit can be made simple in structure, and inexpensive.

The voltage and the frequency applied to the high-frequency wire 22 for the self-cleaning unit may be the same as applied to the summarizing section 5 and the analyzing section 7. The frequency thereof is from several hundreds of megahertz to several gigahertz. Self-cleaning and analysis/measurement are not simultaneously attained so that the high-frequency power supply section 12, and the high-voltage power supply section 13 are not increased in electrical capacity. Thus, the existent arithmetic control unit 17, power supply control section 16, high-frequency power supply section 12, and high-voltage power supply section 13 can be used.

A space where the specimen introducing section electrode 2 and the first-pore-section-forming member 3 are located oppositely to each other is used as a specimen-introduction regulating chamber. This specimen-introduction regulating chamber has therein a pressure equivalent to the atmospheric pressure. A space where the first-pore-section-forming member 3 and the second-pore-section-forming member 4 are located oppositely to each other is used as a differential evacuation chamber (interface chamber). A space where the second-pore-section-forming member 4 is located oppositely to a third-pore-section-forming member 6 having at the center thereof a third pore is used as a summarizing chamber. At the downstream side of the summarizing chamber, an analyzing chamber having the analyzing section is located. The differential evacuation chamber has therein a pressure of about 200 Pa. The pressure in the specimen-introduction regulating chamber, as well as that in the differential evacuation chamber, is not substantially varied between the time of the analysis/measurement and that of the cleaning-up. The pressure in the summarizing chamber, as well as that in the analyzing chamber, is equivalent to that in the differential evacuation chamber, or 200 Pa or less.

The pore made in the specimen introducing section electrode 2, the first pore made in the first-pore-section-forming member 3, and the second pore made in the second-pore-section-forming member 4 each have a pore diameter of 0.1 to 2 mm. Ions of any specimen are caused to flow through these pores to analyze/measure the specimen.

A specimen to be analyzed is supplied by the analysis-specimen supplying section (LC) 11, and the supplied specimen is introduced into the specimen ionizing unit 1. Reference number 9 represents an analysis-specimen jetting-out section. The specimen is ionized by the specimen ionizing unit 1, and the ionized specimen is fed into the vicinity of the specimen introducing section of the mass spectrometry device. The specimen is then introduced into the mass spectrometry device through the pore in the specimen introducing section electrode 2, the first pore in the first-pore-section-forming member 3, and the second pore in the second-pore-section-forming member 4 to each of which a voltage is applied (not illustrated) by effect of the power supply control section 16 controlled by the arithmetic control unit 17, and the high-voltage power supply section 13 controlled by the power supply control section 16. The ions accelerated or decelerated by the application of the voltage are advanced to a lens system located back.

The ion group (beam) 26 introduced in the mass spectrometry device is caused to converge or diverge by the following: the power supply control section 16 controlled by the arithmetic control unit 17; the high-frequency power supply section 12 controlled by the power supply control section 16; the summarizing section 5 and the analyzing section 7 to each of which a voltage is applied by the high-voltage power supply section 13; and the third-pore-forming member 6 having at the center thereof the third pore, to which a voltage is applied by the power supply control section 16 controlled by the arithmetic control unit 17, and the high-voltage power supply section 13 controlled by the power supply control section 16. As a result, an unnecessary region of the ion group (beam) 26 is removed.

Thereafter, the ion group (beam) 26 subjected to the mass separation by the analyzing section 7 is introduced into the detector 10 of the detecting section 8 to which a voltage is applied by effect of the power supply control section 16 controlled by the arithmetic control unit 17, and the detecting section power supply section 14 controlled by the power supply control section 16. The ion group (beam) 26 introduced in the detector 10 is amplified by the signal amplifier 15, and then subjected to arithmetic processing by the arithmetic control unit 17. Thereafter, an analysis result specified therefrom is displayed in the analysis-result displaying device 18.

In the present example, when the specimen ionized by the specimen ionizing unit 1 is an insufficiently ionized specimen, the specimen remains near the introducing section electrode 2, the first-pore-section-forming member 3, and the second-pore-section-forming member 4 and then the specimen is deposited as a product such as an oxide or carbide by an energy such as heat.

Figure 2:
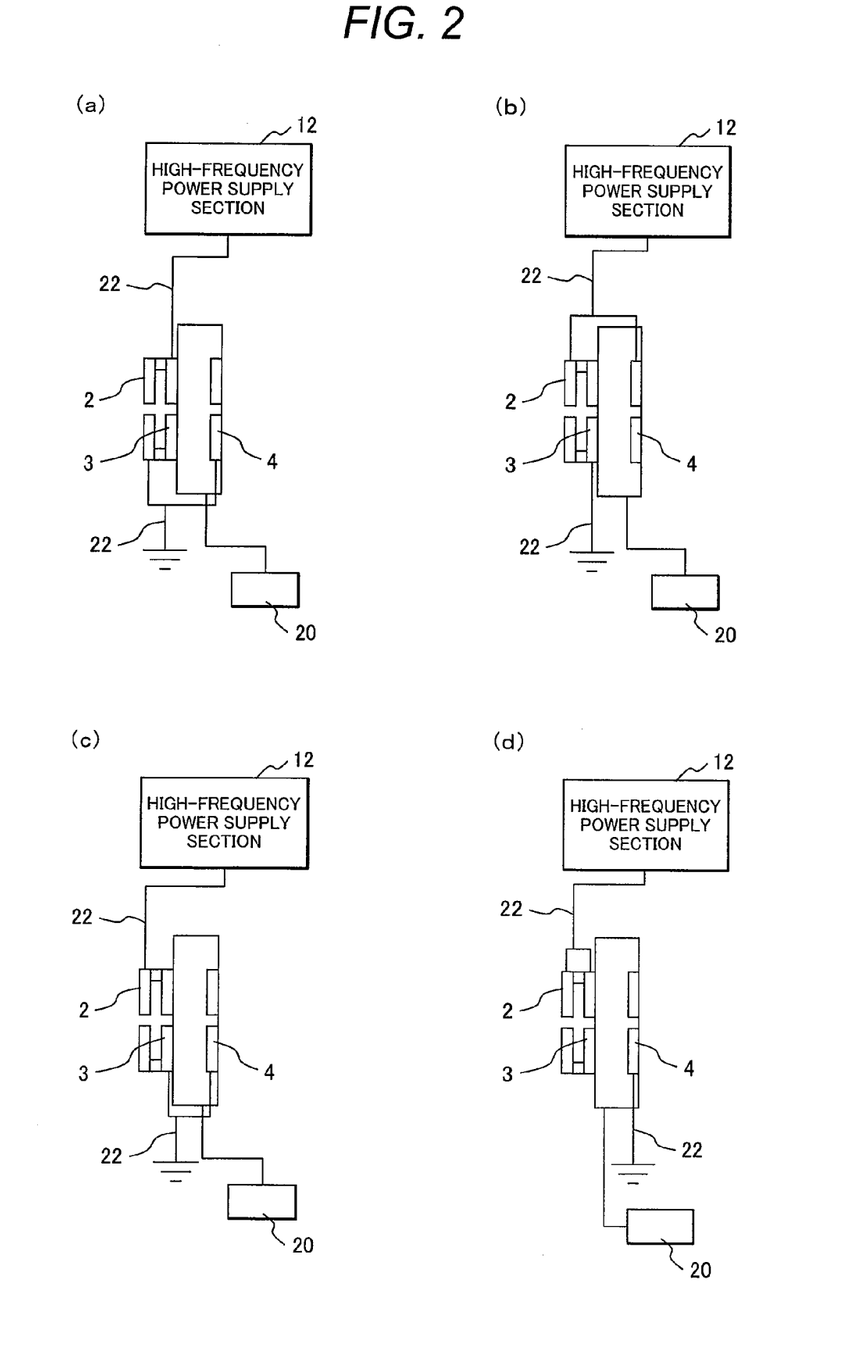
FIG. 2 are each view illustrating a structure in which an existent or newly set-up high-frequency power supply is laid out to configure a self-cleaning unit in an example of the invention (illustrated is only an interface corresponding to preceding members of the mass spectrometry device).

The deposited product narrows the pore in the specimen introducing section of the mass spectrometry device, and the deposit is electrically charged onto the part or component surface. By these inconveniences and others, the mass spectrometry device is deteriorated in performance to cause a problem. As illustrated in FIGS. 1 and 2, the following are configured: the power supply control section 16 controlled by the arithmetic control unit 17, which is composed of existent components; the high-frequency power supply section 12 controlled by the power supply control section 16; and a self-cleaning unit for supplying a potential supplied from the high-frequency power supply section 12, through the high-frequency wire 22 for the self-cleaning unit, to the specimen introducing section electrode 2, the first-pore-section-forming member 3 and the second-pore-section-forming member 4 that are efficiently arranged.

Self-cleaning is performed to reform a stationary state that the mass spectrometry device is deteriorated in performance to require maintenance. The deposit decomposed by the high-frequency energy is discharged as an effluent gas discharged at an atomic or molecular level at the time of the cleaning. The deposit is discharged by a fan for discharging any gas mainly at the moieties for promoting the ionization or the pump 20 for rough pressure-reduction.

In order to detect the end point thereof, the deposit decomposed by the high-frequency energy is taken into the mass spectrometry device at an atomic or molecular level and the atmosphere therein is detected by a function of the mass spectrometry device while the device is cleaned. In this way, the end point for verifying the effect of the cleaning can be detected. The self-cleaning provides a stable device performance of the mass spectrometry device.

Alternatively, the following are configured: the power supply control section 16 controlled by the arithmetic control unit 17, which is formed separately from the mass spectrometry device; the high-frequency power supply section 12 controlled by the power supply control section 16; and a self-cleaning unit for supplying a potential supplied from the high-frequency power supply section 12 to the specimen introducing section electrode 2, the first-pore-section-forming member 3 and the second-pore-section-forming member 4 that are efficiently arranged. Self-cleaning is performed to reform a stationary state that the mass spectrometry device is deteriorated in performance to require maintenance.

The deposit decomposed by the high-frequency energy is discharged as an effluent gas discharged at an atomic or molecular level at the time of the cleaning. The deposit is discharged by a fan for discharging any gas mainly at the moieties for promoting the ionization or the pump 20 for rough pressure-reduction. In order to detect the end point thereof, the deposit decomposed by the high-frequency energy is taken into the mass spectrometry device at an atomic or molecular level and the atmosphere therein is detected by a function of the mass spectrometry device while the device is cleaned. In this way, the end point for verifying the effect of the cleaning can be detected. The self-cleaning provides a stable device performance of the mass spectrometry device.

In each of FIG. 2, a specimen introducing section electrode (counter plate or curtain plate: electrode) 2, a first-pore-section-forming member (AP1: electrode) 3, and a second-pore-section-forming member (AP2: electrode) 4, which are arranged in such a mass spectrometry device, are taken up as an exemplification. FIG. 2 illustrate examples in each of which a high-frequency power supply is connected to the electrodes opposed to each other in such a manner that its positive and negative electrode form a pair. FIG. 2(a) illustrates one of the examples in which a positive potential is connected to the first-pore-section-forming member (AP1: electrode) 3, and a negative potential is connected to the specimen introducing section electrode (counter plate or curtain plate: electrode) 2 and the second-pore-section-forming member (AP2: electrode) 4, which are arranged in the mass spectrometry device.

FIG. 2(b) illustrates one of the examples in which a positive potential is connected to the specimen introducing section electrode (counter plate or curtain plate: electrode) 2 and the second-pore-section-forming member (AP2: electrode) 4, which are arranged in the mass spectrometry device, and a negative potential is connected to the first-pore-section-forming member (AP1: electrode) 3. FIG. 2(c) illustrates one of the examples in which a positive electrode is connected to the specimen introducing section electrode (counter plate or curtain plate: electrode) 2, which is arranged in the mass spectrometry device, and a negative electrode is connected to the first-pore-section-forming member (AP1: electrode) 3, and the second-pore-section-forming member (AP2: electrode) 4.

FIG. 2(d) illustrates one of the examples in which a positive electrode is connected to the specimen introducing section electrode (counter plate or curtain plate: electrode) 2, and the first-pore-section-forming member (AP1: electrode) 3, which are arranged in the mass spectrometry device, and a negative electrode is connected to the second-pore-section-forming member (AP2: electrode) 4.

On the basis of each of the arrangement examples of the electrodes, from the existent high-frequency power supply 12 or the newly set-up high-frequency power supply 12, a potential is supplied through the high-frequency wire 22 for the self-cleaning unit to generate a glow discharge, whereby a self-cleaning unit is created.

The present examples also each provide a mass spectrometry device in which a self-cleaning unit is configured, this unit being a unit in which cleaning can be performed while for verifying the effect of the cleaning a function of the mass spectrometry device is used to check the spectrum of a specific deposit.

Figure 7:
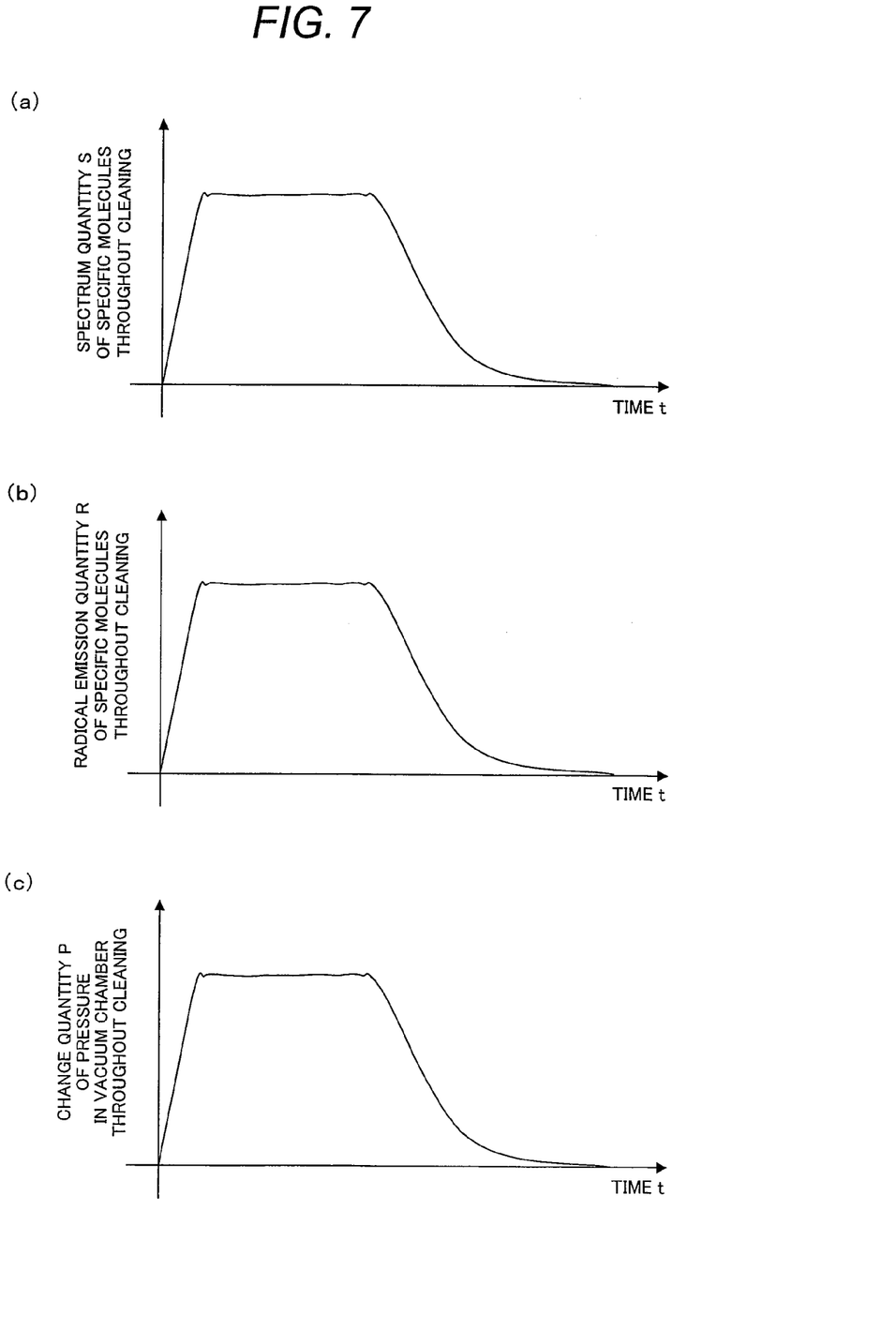
FIG. 7 are each a graph showing a change quantity (spectrum, radicals or vacuum pressure) of specific molecules while the molecules are cleaned up in an example of the invention.

As shown in FIG. 7(a), the specific spectrum is changed with the passage of time t; thus, in order to verify the effect of the cleaning in the mass spectrometry device, the end point of the cleaning is detected by regarding the change as the end point.

Figure 8:
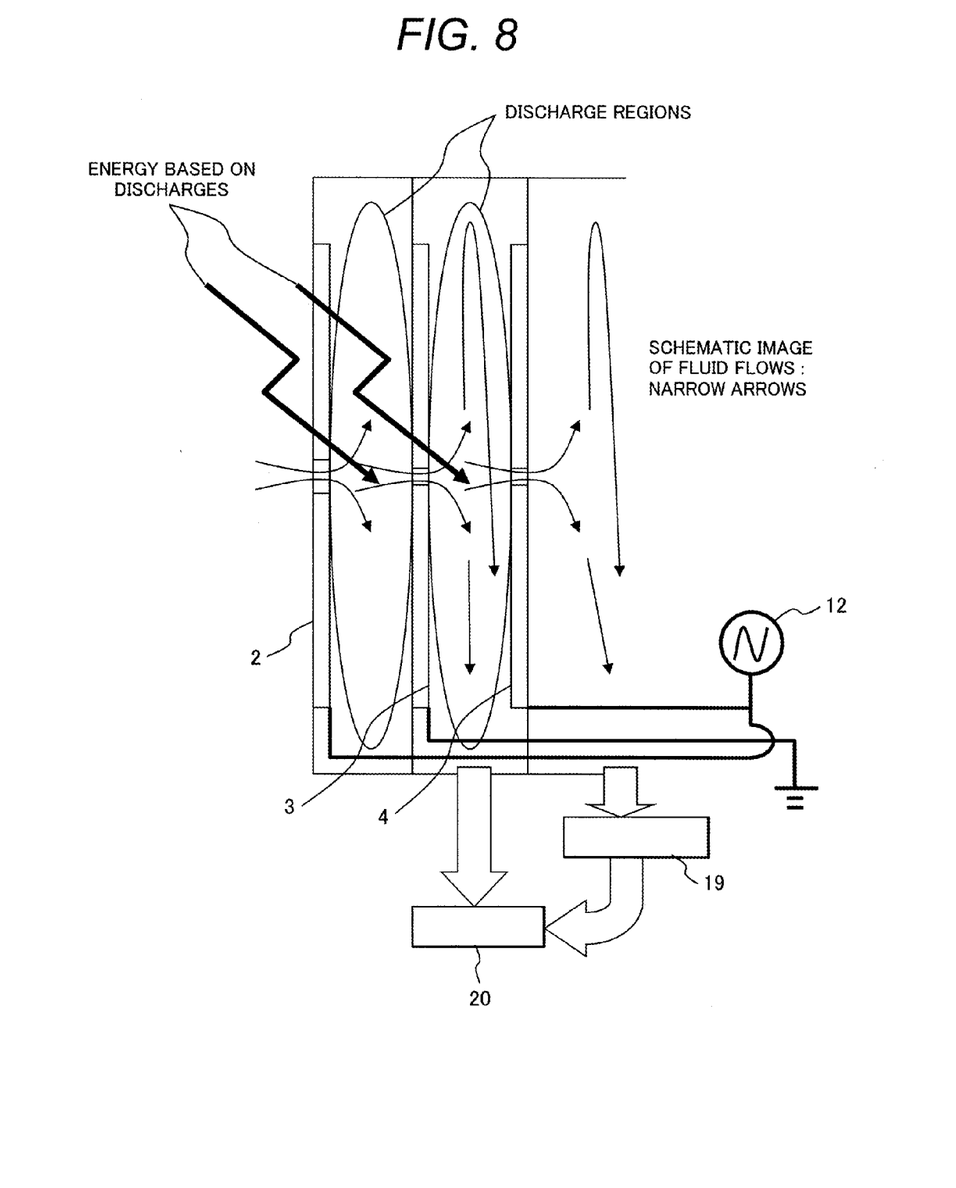
FIG. 8 is a view illustrating schematically a decomposition of a deposit by a glow discharge in an example of the invention.

The cleaning will be further described with reference to FIG. 8, which schematically illustrates the cleaning.

A voltage from the high-frequency power supply section 12 is applied to the specimen introducing section electrode 2, the first-pore-section-forming member 3 (electrode), in which the first pore is made, and the second-pore-section-forming member 4 (electrode), in which the second pore is made. The specimen introducing section electrode 2 and the second-pore-section-forming member 4 (electrode) function as a positive electrode. The first-pore-section-forming member 3 (electrode) functions as a negative electrode. In the cleaning, a high-frequency voltage is applied to the specimen introducing section electrode 2, the second-pore-section-forming member 4 (electrode), and the first-pore-section-forming member 3 (electrode) while evacuation is performed by the pump 20 for rough pressure-reduction and the high-vacuum pump 19.

By the application of the high-frequency voltage, a glow discharge is generated in each of the specimen-introduction regulating chamber in which the specimen introducing section electrode 2 and the first-pore-section-forming member 3 (electrode) are opposed to each other, and the differential evacuation chamber (interface chamber) in which the first-pore-section-forming member 3 (electrode) and the second-pore-section-forming member 4 (electrode) are opposed to each other. A discharge region of the glow discharge extends over substantially the whole of the pore in the specimen introducing section electrode 2, the first pore, the second pore, the specimen-introduction regulating chamber, and the differential evacuation chamber.

The discharge energy acts onto a deposit adhering and depositing on the surfaces of the pore in the specimen introducing section electrode 2, the first pore, the second pore, the specimen-introduction regulating chamber, and the differential evacuation chamber, so that the deposit is decomposed into fine pieces. The pieces are absorbed by the pump 20 for rough pressure-reduction and the high-vacuum pump 19 to be discharged, together with the effluent gas, outside from the specimen-introduction regulating chamber, the differential evacuation chamber, and the summarizing chamber. The air flowing in the pore in the specimen introducing section electrode 2, the first pore and the second pore is caused to flow circularly inside the specimen-introduction regulating chamber, the differential evacuation chamber and the analyzing chamber, as represented by arrows. The finely decomposed deposit rides on the circular flow to be absorbed by the pump 20 for rough pressure-reduction and the high-vacuum pump 19, thereby being discharged. For this reason, the deposit adhering and depositing on the surfaces of the pores in the specimen introducing section electrode 2, the first pore, the second pore, the specimen-introduction regulating chamber and the differential evacuation chamber are satisfactorily cleaned up, so that the mass spectrometry device can stably keep analysis/measurement performance.

Since the existent pump 20 for rough pressure-reduction and high-vacuum pump 19, which the mass spectrometry device has, are used, the structure of the mass spectrometry device is not made complicated to be inexpensive.

Example 2

Figure 3:
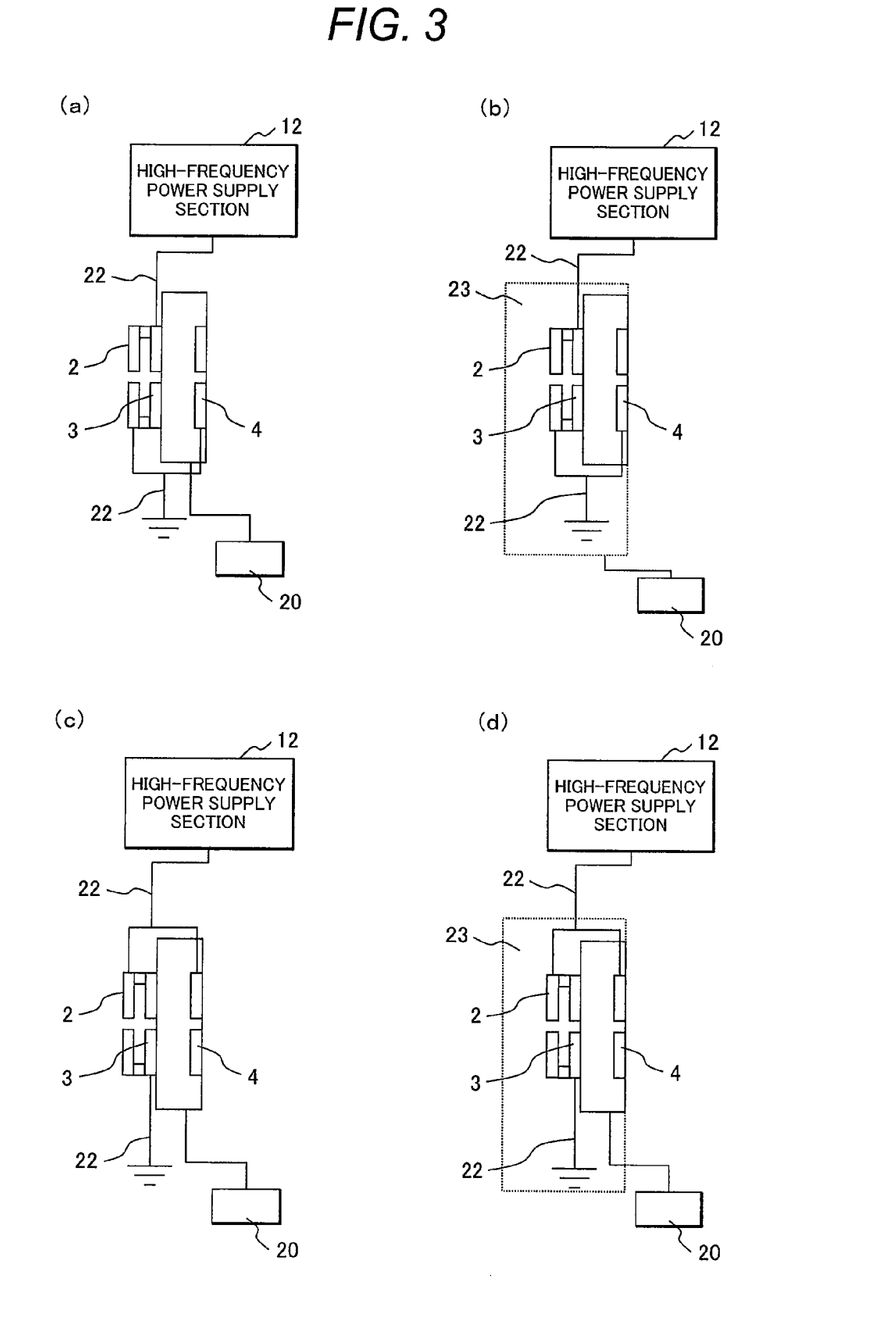
FIG. 3 are each a view illustrating a structure in which a high-frequency power supply is laid out in an atmospheric pressure environment or a vacuum pressure environment to configure a self-cleaning unit in an example of the invention (illustrated is only an interface corresponding to preceding members of the mass spectrometry device).

In present Example, a description is made about examples of a self-cleaning unit in which self-cleaning can be performed in a vacuum in the state of locating, into the atmospheric air, an atmosphere for self-cleaning the vicinity of sites extending from the specimen ionizing unit 1 of the mass spectrometry device through the specimen introducing section electrode 2 and the first-pore-section-forming member 3 to the second-pore-section-forming member 4, or of locating, into a vacuum atmosphere in a vacuum vessel 23 for the self-cleaning unit, the vicinity of sites to be self-cleaned, which are the specimen introducing section electrode 2, the first-pore-section-forming member 3 and the second-pore-section-forming member 4. The pressure in the vacuum vessel 23 for the self-cleaning unit is a substantially middle pressure between 200 Pa and the atmospheric pressure. The specimen introducing section electrode 2, the specimen ionizing unit 1, and the analysis-specimen supplying section (LC) 11 may be covered with an atmospheric pressure vessel. The pressure in the atmospheric pressure vessel is approximately the atmospheric pressure.

FIG. 3 are respective structural view examples illustrating self-cleaning units in Example 2.

In FIG. 3, about portions or components which each have the same function as the structure to which the same reference number as in the mass spectrometry device shown in the figure which has already been described, FIG. 1, is attached, description is partially omitted.

FIGS. 3(a) and 3(c) each illustrate a case where one of the cleaning units formed in Example 2 is laid out in the atmosphere on the basis of the electrode arrangement example illustrated in FIG. 2(a). FIGS. 3(b) and 3(d) each illustrate a case where one of the cleaning units formed in Example 2 is located in a vacuum vessel on the basis of the electrode arrangement example illustrated in FIG. 2(b). In the atmospheric environment also, a cleaning effect can be gained by generating a glow discharge phenomenon. In order to gain a more stable glow discharge, a glow discharge phenomenon in the vacuum atmosphere is stably supplied so that a stable cleaning effect is obtained.

A deposit decomposed by the self-cleaning is discharged as an effluent gas discharged at an atomic or molecular level at the time of the cleaning. The deposit is discharged by a fan for discharging any gas mainly at the moieties for promoting the ionization or the pump for rough pressure-reduction. In order to detect the end point thereof, the deposit decomposed by the high-frequency energy is taken into the mass spectrometry device at an atomic or molecular level, and the atmosphere therein is detected by a function of the mass spectrometry device while the device is cleaned. In this way, the end point for verifying the effect of the cleaning can be detected.

Example 3

Figure 4:
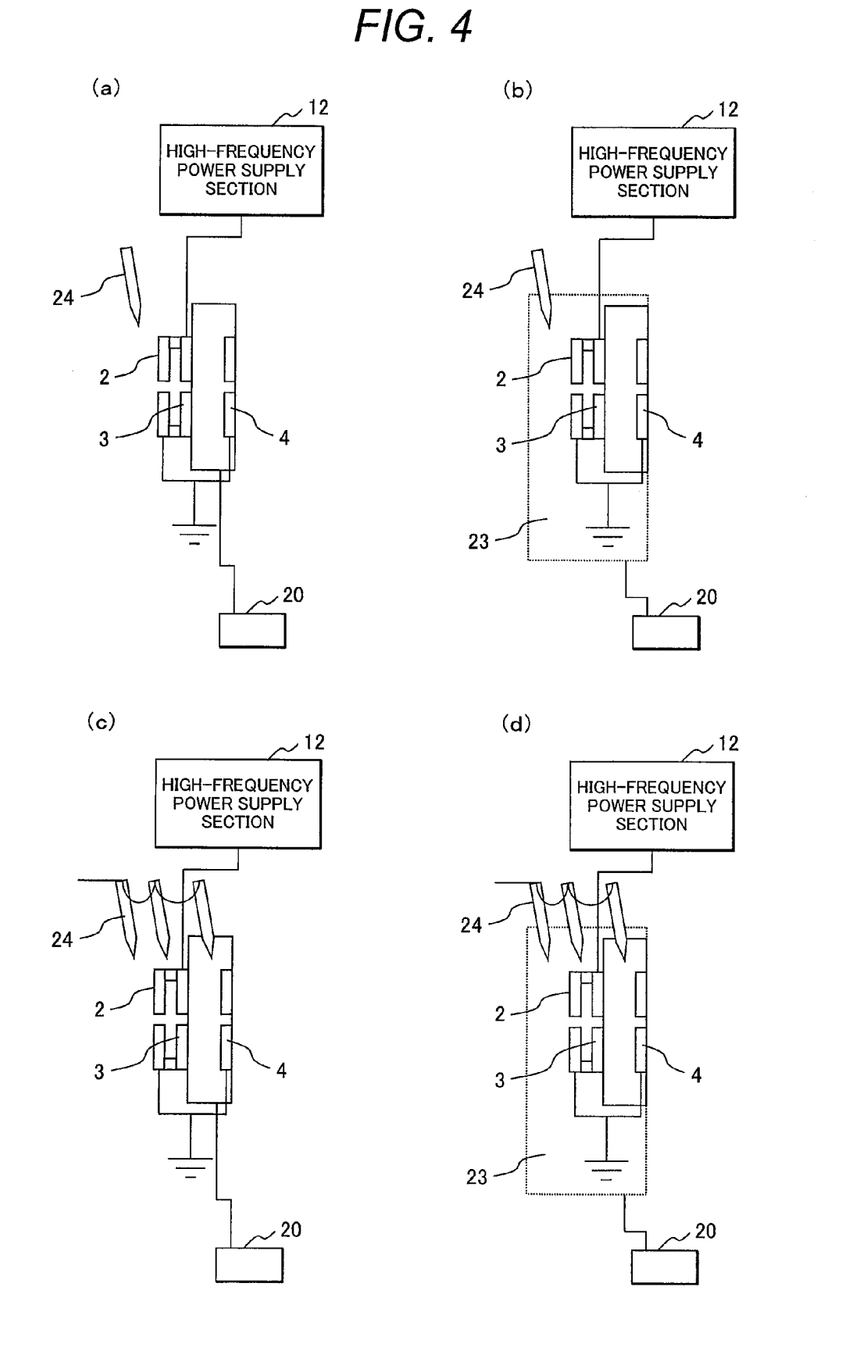
FIG. 4 are each a view illustrating a structure in which an auxiliary gas or chemical liquid is introduced in an atmospheric pressure environment or a vacuum pressure environment, and a high-frequency power supply is laid out to configure a self-cleaning unit in an example of the invention (illustrated is only an interface corresponding to preceding members of the mass spectrometry device).

In present Example, a description is made about examples of a self-cleaning unit in which self-cleaning can be performed in a vacuum in the state of locating, into the atmospheric air, an atmosphere for self-cleaning the vicinity of sites extending from the specimen ionizing unit 1 of an ordinary mass spectrometry device through the specimen introducing section electrode 2 and the first-pore-section-forming member 3 to the second-pore-section-forming member 4, or of locating, into a vacuum atmosphere in a vacuum vessel 23 for the self-cleaning unit, the vicinity of sites to be self-cleaned, which are the specimen introducing section electrode 2, the first-pore-section-forming member 3 and the second-pore-section-forming member 4; and further the self-cleaning can be performed in the state of arranging one or more introducing sections 24 for an auxiliary gas or chemical liquid for heightening the cleaning effect.

FIG. 4 are respective structural view examples illustrating self-cleaning units in Example 2.

In FIGS. 4, about portions or components which each have the same function as the structure to which the same reference number as in the mass spectrometry devices shown in the figures which have already been described, FIGS. 1 to 3, is attached, description is partially omitted.

FIG. 4(a) illustrates a case where one of the self-cleaning units formed in Example 2 is laid out in the atmosphere, and the introducing section 24, for an auxiliary gas or chemical liquid for heightening the cleaning effect, is arranged.

FIG. 4(b) illustrates a case where the same self-cleaning unit formed in Example 2 is laid out in a vacuum vessel, and the introducing section 24, for an auxiliary gas or chemical liquid for heightening the cleaning effect, is arranged.

FIG. 4(c) illustrates a case where one of the self-cleaning units formed in Example 2 is laid out in the atmosphere, and the introducing sections 24, for an auxiliary gas or chemical liquid for heightening the cleaning effect, are arranged.

FIG. 4(d) illustrates a case where one of the self-cleaning unit formed in Example 2 is laid out in a vacuum vessel, and the introducing sections 24, for an auxiliary gas or chemical liquid for heightening the cleaning effect, are arranged.

In some of the self-cleaning units, a glow discharge phenomenon is generated in the atmospheric environment to gain a cleaning effect. In order to gain a more stable glow discharge (in the others), a glow discharge phenomenon in the vacuum atmosphere is stably supplied to gain a stable cleaning effect.

A deposit decomposed by the self-cleaning is discharged as an effluent gas discharged at an atomic or molecular level at the time of the cleaning. The deposit is discharged by a fan for discharging any gas mainly at the moieties for promoting the ionization or the pump for rough pressure-reduction. In order to detect the end point thereof, the deposit decomposed by the high-frequency energy is taken into the mass spectrometry device at an atomic or molecular level and the atmosphere therein is detected by a function of the mass spectrometry device while the device is cleaned. In this way, the end point for verifying the effect of the cleaning can be detected.

Example 4

Figure 5:
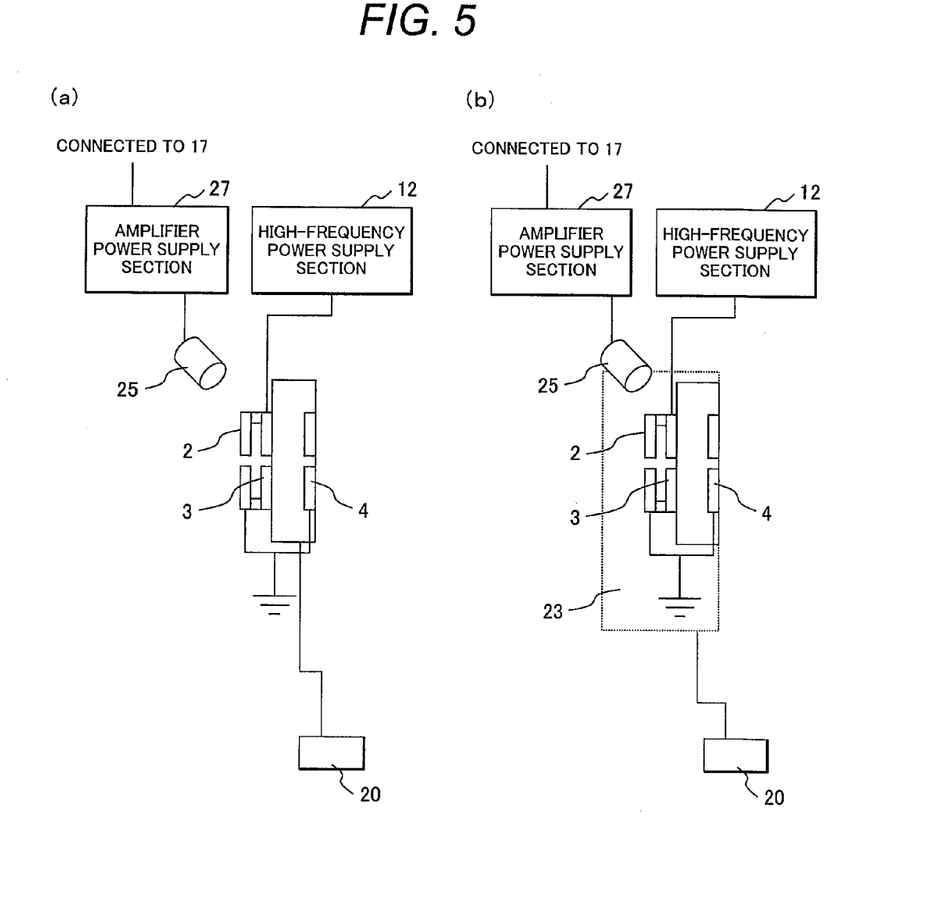
FIG. 5 are each a view illustrating a structure in which an optical detector such as a spectroscope or plasma monitor is set and a high-frequency power supply is laid out to configure a self-cleaning unit in an example of the invention (illustrated is only an interface corresponding to preceding members of the mass spectrometry device).

In present Example, a description is made about examples of a self-cleaning unit in which self-cleaning can be performed in a vacuum in the state of locating, into the atmospheric air, an atmosphere for self-cleaning the vicinity of sites extending from the specimen ionizing unit 1 of an ordinary mass spectrometry device through the specimen introducing section electrode 2 and the first-pore-section-forming member 3 to the second-pore-section-forming member 4, or of locating, into a vacuum atmosphere in a vacuum vessel 23 for the self-cleaning unit, the vicinity of sites to be self-cleaned, which are the specimen introducing section electrode 2, the first-pore-section-forming member 3 and the second-pore-section-forming member 4; and further the self-cleaning can be performed in the state of arranging a detector 25 such as a spectroscope or plasma monitor for checking a cleaning effect.

FIG. 5 are respective structural view examples illustrating self-cleaning units in Example 4.

In FIGS. 5, about portions or components which each have the same function as the structure to which the same reference number as in the mass spectrometry devices shown in the figures which have already been described, FIGS. 1 to 4, is attached, description is partially omitted.

For verifying the effect of cleaning in each of the present examples, while a function of a mass spectrometry device is used to check the mass spectrum of a specific deposit, the cleaning can be performed. However, in the case of desiring to heighten an advantageous effect of the detection of the cleaning effect, the following are configured: an end-point-detector 25 for a self-cleaning unit, such as a spectroscope or a plasma monitor; an amplifier for the end-point-detector for the self-cleaning unit (the spectroscope or plasma monitor); and a power supply section 27. In such a way, provided is a mass spectrometry device having a self-cleaning unit in which the detection of an end point of self-cleaning is made high in precision.

FIG. 5 each illustrate a case in which the sections above an amplifier power supply section 27 for the end-point-detector for the self-cleaning unit (the spectroscope or plasma monitor) and in present Example are shared by an arithmetic control unit 17 and a specimen image displaying device (analysis-result displaying device) 18 of a mass spectrometry device. However, a different arithmetic control unit and displaying section may be separately configured.

As shown in FIG. 7(b), a specific radical emission quantity is changed with the passage of time t; thus, in order to verify the effect of cleaning in the mass spectrometry device, the end point of the cleaning is detected by regarding the change as the end point.

A deposit decomposed by the self-cleaning is discharged as an effluent gas discharged at an atomic or molecular level at the time of the cleaning. The deposit is discharged by a fan for discharging any gas mainly at the moieties for promoting the ionization or the pump for rough pressure-reduction.

Example 5

Figure 6:
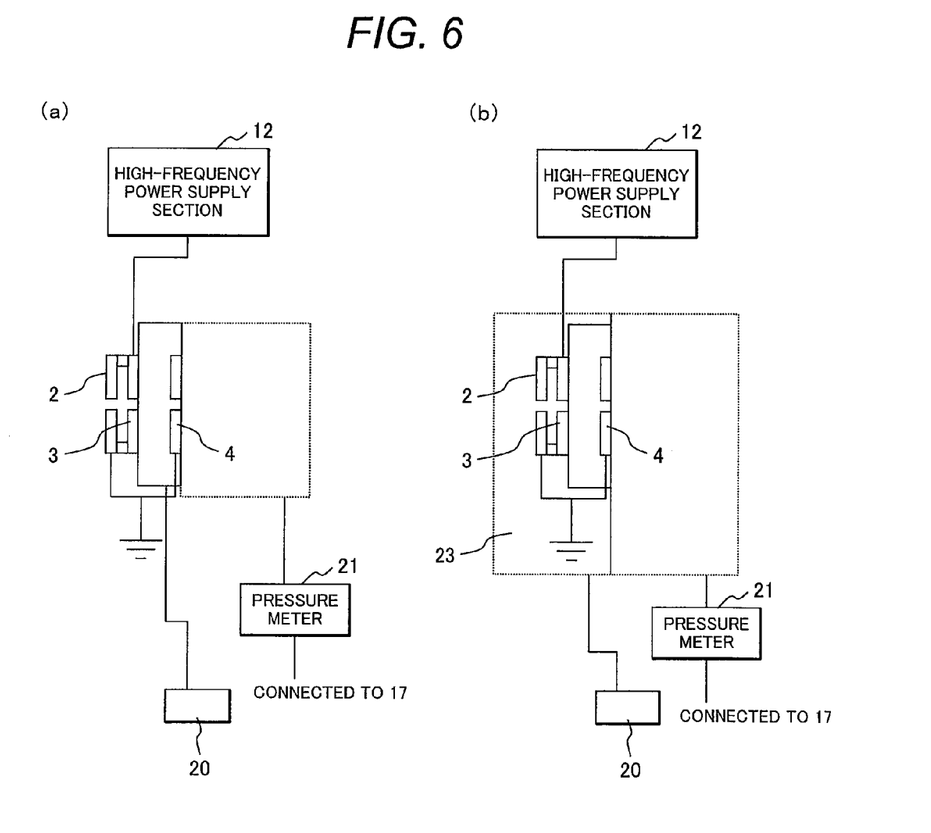
FIG. 6 are each a view illustrating a structure in which an existent or newly set-up pressure meter is set and a high-frequency power supply is laid out to configure a self-cleaning unit in an example of the invention (illustrated is only an interface corresponding to preceding members of the mass spectrometry device).

In present Example, a description is made about examples of a self-cleaning unit in which self-cleaning can be performed in a vacuum in the state of locating, into the atmospheric air, an atmosphere for self-cleaning the vicinity of sites extending from the specimen ionizing unit 1 of an ordinary mass spectrometry device through the specimen introducing section electrode 2 and the first-pore-section-forming member 3 to the second-pore-section-forming member 4, or of locating, into a vacuum atmosphere in a vacuum vessel 23 for the self-cleaning unit, the vicinity of sites to be self-cleaned, which are the specimen introducing section electrode 2, the first-pore-section-forming member 3 and the second-pore-section-forming member 4; and further the self-cleaning can be attained in the state of arranging, for example, a pressure meter 21 for verifying the effect of the cleaning.

FIG. 6 are respective structural view examples illustrating self-cleaning units in Example 5.

In FIGS. 6, about portions or components which each have the same function as the structure to which the same reference number as in the mass spectrometry devices shown in the figures which have already been described, FIGS. 1 to 5, is attached, description is partially omitted.

The present examples also each provide a mass spectrometry device having a self-cleaning unit in which cleaning can be performed while for verifying the effect of the cleaning a function of the mass spectrometry device is used to check the spectrum of a specific deposit.

As shown in FIG. 7(c), the pressure in the vacuum chamber is changed peculiarly to the cleaning with the passage of time t; thus, in order to verify the effect of the cleaning in the mass spectrometry device, the end point of the cleaning is detected by regarding the change as the end point. Examples of a detecting means for detecting the end point of the cleaning for detecting the end point of the cleaning include a spectroscope, a plasma monitor, other optical units, and a pressure meter.

When a pressure of zero is regarded as the vacuum, this change P in the pressure in the vacuum chamber demonstrates that: a substance present as a deposit stabilized at a molecular level is decomposed at an atomic or molecular level by giving discharge energy thereto, and thus the decomposition product is present in an unstable state in the vacuum so that the vacuum is transitionally lost; and when the deposit has been lost, the inside in the chamber is returned in the vacuum, in which the pressure is zero. The period when the change P in the pressure in the vacuum chamber is shifted or transited is from several seconds to several tens of seconds.

The deposit decomposed by the self-cleaning is discharged as an effluent gas discharged at an atomic or molecular level at the time of the cleaning. The deposit is discharged by a fan for discharging any gas mainly at the moieties for promoting the ionization or the pump for rough pressure-reduction.

The effect of decomposing the deposit can be heightened by generating a glow discharge while a reactive gas (etching gas) or washing liquid for promoting the decomposition of the deposit by the glow discharge is introduced.

In the above-mentioned examples, glow discharges are generated, respectively, between the introducing electrode and the first-pore-section-forming member (electrode) opposed to each other in the specimen-introduction regulating chamber, between the first-pore-section-forming member (electrode) and the second-pore-section-forming member (electrode) opposed to each other in the differential evacuation chamber, and between the second-pore-section-forming member (electrode) and the third-pore-section-forming member (electrode) opposed to each other in the summarizing chamber. However, a means (such as an arc discharge) other than the discharge generating means (self-cleaning unit), in which two of these electrodes are opposite to each other, may be used. A discharge can be generated by means of only electrodes.

As described above, the invention is characterized by the following: when a mass spectrometry device is maintained to remove a product, such as an oxide or carbide, generated in the vicinity of a specimen introducing section of the device, the deposited product is decomposed and removed by a glow discharge energy based on high frequency (RF) excitation, which is performed without requiring detaching and attaching operations of maintenance parts, the cancel of the vacuum, the stop of supplying electric power to its heater or heat source, the re-supply of electric power thereto, nor other operations; and thus the device-starting-up period after the maintenance is shortened, and after the maintenance the device is made into more stable state.

Moreover, the state of the cleaning effect is also verified by use of a function of the mass spectrometry device that the atmosphere in its vacuum chamber is subjected to mass spectrometry while the cleaning is made. Alternatively, the method for the verification may be a method of detecting the end point thereof from a change in a specific signal intensity with the passage of time, such as a method of arranging, for example, a detector for detecting the quantity of a light ray having a specific wavelength through a spectroscope, a plasma monitor or some other; or a method of detecting the end point through a change in the pressure. Each of the methods is characterized in that the end point for verifying the cleaning effect is detected by measurement through the quadrupole mass spectrometry device, a spectrometer, a pressure meter, or some other. When the measurement made through the pressure meter is made in the vacuum chamber, the pressure measurement can be attained in the differential evacuation chamber or analyzing chamber. A pressure fluctuation measured through the pressure meter is a fluctuation from the base pressure in the vacuum chamber.

Although the maintenance of any mass spectrometry device involves the dismantlement of parts of the device, the fabrication thereof, the cancel of the vacuum, vacuum-drawing, and other works so that the maintenance requires a predetermined period in one day, the present invention makes it possible to shorten the maintenance period since the present self-cleaning, which can be performed when the device is in a stationary state, does not require any period until the heat source and the vacuum degree are stabilized after the maintenance work. Moreover, at the time of the maintenance, the environment around the mass spectrometry device is not broken, so that after the maintenance the device continuously keeps a stable performance in a stable environment. As a result, the device makes it possible to lighten or reduce problems based on deterioration in the performance thereof, or on others.

REFERENCE SIGNS LIST

1 . . . specimen ionizing unit (ion source), 2 . . . specimen introducing section electrode (counter plate or curtain plate:

electrode), 3 . . . first-pore-section-forming member (AP1: electrode), 4 . . . second-pore-section-forming member (AP2: electrode), 5 . . . summarizing section (QO: summarizer/electrode pole), 6 . . . third-pore-section-forming member (AP3: electrode), 7 . . . quadrupole mass spectrometry device analyzing section, 8 . . . detecting section, 9 . . . analysis-specimen jetting-out section, 10 . . . detector, 11 . . . analysis-specimen supplying section (LC), 12 . . . high-frequency power supply section, 13 . . . high-voltage power supply section, 14 . . . detector power supply section, 15 . . . signal amplifier, 16 . . . power supply control section, 17 . . . arithmetic control unit, 18 . . . analysis-result displaying device, 19 . . . high-vacuum pump (such as turbo motor), 20 . . . pump for rough pressure-reduction (such as motor pump), 21 . . . pressure meter, 22 . . . high-frequency wire for a self-cleaning unit, 23 . . . a vacuum vessel for the self-cleaning unit, 24 . . . section for introducing an auxiliary gas or chemical liquid for the self-cleaning unit, 25 . . . end-point detector (spectroscope or plasma monitor) for the self-cleaning unit, 26 . . . ion group (beam), and 27 . . . amplifier power supply section for the end-point detector (spectroscope or plasma monitor) for the self-cleaning unit

The invention claimed is:

1. A mass spectrometry device, comprising a specimen supply source, a specimen ionizing section for ionizing a specimen supplied from the specimen supply source, a specimen-introduction regulating chamber into which ions of the ionized specimen are introduced, a differential evacuation chamber located at the downstream side of the specimen-introduction regulating chamber, and an analyzing section located at the downstream side of the differential evacuation chamber,
the device further comprising a discharge generating means for generating an electric discharge inside at least one of the specimen-introduction regulating chamber and the differential evacuation chamber,
wherein the discharge generating means uses a high-frequency.

2. The mass spectrometry device according to claim 1,
wherein the discharge generating means has a specimen introducing section electrode and a first-pore-section-forming member, which is an electrode, located oppositely to each other inside the specimen-introduction regulating chamber, or a first-pore-section-forming member, which is an electrode, and a second-pore-section-forming member, which is an electrode, located oppositely to each other inside the differential evacuation chamber.

3. The mass spectrometry device according to claim 2,
further comprising an atmospheric pressure vessel for covering the specimen introducing section electrode, the specimen ionizing section, and the specimen supply source.

4. The mass spectrometry device according to claim 2,
further comprising a vacuum pressure vessel for covering the specimen introducing section electrode, the first-pore-section-forming member, which is an electrode, the second-pore-section-forming member, which is an electrode, and the differential evacuation chamber.

5. The mass spectrometry device according to claim 1,
wherein the electric discharge is continued while a gas or washing liquid for promoting the decomposition of a deposit is introduced.

6. The mass spectrometry device according to claim 1,
further comprising a detecting means for detecting an end point of cleaning by the electric discharge using the high-frequency,
wherein the detecting means detects an end point of cleaning by verifying a mass spectrum of a specific deposit.

7. The mass spectrometry device according to claim 6,
wherein the detecting means for detecting the end point of cleaning comprises a self-cleaning unit including an optical unit such as a spectroscope or a plasma monitor.

8. The mass spectrometry device according to claim 6,
wherein the detecting means for detecting the end point of cleaning comprises a self-cleaning unit including a pressure meter.

* * * * *